United States Patent [19]

Van Den Berg

[11] Patent Number: 5,824,789
[45] Date of Patent: Oct. 20, 1998

[54] HUMAN GROWTH FACTORS, NUCLEOTIDE SEQUENCE ENCODING GROWTH FACTORS, AND METHOD OF USE THEREOF

[75] Inventor: David John Van Den Berg, Sunnyvale, Calif.

[73] Assignee: SyStemix, Inc., Palo Alto, Calif.

[21] Appl. No.: 485,449

[22] Filed: Jun. 7, 1995

[51] Int. Cl.$^6$ .......................... C12N 15/18; C12N 15/63
[52] U.S. Cl. .................... 536/23.5; 435/69.1; 435/320.1; 435/365.1
[58] Field of Search .................... 536/23.5; 435/69.1, 435/365.1, 320.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,754,065 | 6/1988 | Levenson et al. | 435/254.21 |
| 4,800,159 | 1/1989 | Mullis et al. | 435/91.2 |
| 5,185,438 | 2/1993 | Lemischka | 536/23.2 |
| 5,215,895 | 6/1993 | Bennett et al. | 435/69.52 |
| 5,270,458 | 12/1993 | Lemischka | 536/23.5 |
| 5,304,637 | 4/1994 | Dorssers et al. | 530/351 |
| 5,328,695 | 7/1994 | Lucas et al. | 424/426 |
| 5,371,193 | 12/1994 | Bennett et al. | 530/350 |

FOREIGN PATENT DOCUMENTS

| | | |
|---|---|---|
| 423980 | 4/1991 | European Pat. Off. . |
| 590156 | 4/1994 | European Pat. Off. . |
| 627487 | 12/1994 | European Pat. Off. . |
| WO 90/02183 | 3/1990 | WIPO . |
| WO 91/05795 | 5/1991 | WIPO . |
| WO 91/07499 | 5/1991 | WIPO . |
| WO 92/06707 | 4/1992 | WIPO . |
| WO 92/17505 | 10/1992 | WIPO . |
| WO 93/00349 | 1/1993 | WIPO . |
| WO 93/03061 | 2/1993 | WIPO . |
| WO 93/04169 | 3/1993 | WIPO . |
| WO 93/19660 | 10/1993 | WIPO . |
| WO 93/20197 | 10/1993 | WIPO . |
| WO 94/02593 | 2/1994 | WIPO . |
| 9411510 | 5/1994 | WIPO . |
| WO 94/16718 | 8/1994 | WIPO . |
| WO 95/09912 | 4/1995 | WIPO . |

OTHER PUBLICATIONS

Zsebo et al., "Identification, purification, and biological characterization of hematopoietic stem cell factor from Buffalo Rat liver—conditioned medium" *Cell* (1990), 63:195–201.

Williams et al., "Identification of a ligand for the c–kit proto–oncogene" *Cell* (1990), 63:167–174.

Huang et al. "The hematopoietic growth factor KL is encoded by the Sl locus and is the ligand of the c–kit receptor, the gene product of the W locus" *Cell* (1990), 63:225–233.

Rijsewijk et al. "The Drosophia homolog of the mouse mammary oncogene int–1 is identical to the segment polarity gene wingless" *Cell* (1987), 50:649–657.

Noordermeer et al. "Isolation of the Xenopus homolog of int–1/wingless and expression during nerula stages early development" *Nucl. Acids Res.* (1989), 17:11–18.

Smolich et al. "Wnt family proteins are secreted and associated with the cell surface" *Mol. Biology of the Cell* (1993), 4:1267–1275.

Kanehisa "Use of statistical criteria for screening potential homologies in nucleic acid sequences" *Nucl. Acids Res.* (1984), 12:203–213.

Wetmur et al., "Kinetics of renaturation of DNA" *J. Mol. Biol.* (1968)., 31:349–370.

Metzger et al., "The human oestrogen receptor functions in yeast" *Nature* (1988), 334: 31.

Gluzman et al., eds., "Enhancers and eukaryotic gene expression" *Current Communications in Molecular Biology*, Cold Spring Harbor Press, N.Y. (1983).

Zhu et al., "Systemic gene expression after intravenous DNA delivery into adult mice" *Science* (1993), 261:209–211.

Blasband et al., "The Biochemical Properties and Transforming Potential of Human Wnt–2 are Similar to Wnt–1" *Oncogene* (1992) 7:153–161.

Burrus, "Wnt–1 as a short–range signalling molecule" *BioEssays* (1994) 16:155–157.

Christian et al., "Isolation of cDNAs Partially Encoding Four Xenopus Wnt–1/int–1–Related Proteins and Characterization of their Transient Expression furing Embryonic Development" *Developmental Biology* (1991) 143:230–234.

Clark et al., "Molecular Cloning of the Human Proto–oncogene Wnt–5A and Mapping of the Gene(WNT5A) to Chromosome 3P14–p21" *Genomics* (1993) 18:249–260.

Dickinson et al., "The role of Wnt genes in vertebrate development" *Current Opinion in Genetics and Development* (1992) 2:562–566.

Dickinson et al., "Evidence for a mitogenic effect of Wnt–1 in the developing mammalian central nervous system" *Development* (1994) 120:1453–1471.

Fleischman, "From white spots to stem cells: the role of the Kit receptor in mammalian development" *TIG* (1993) 9:285–290.

Gulati, "Did we focus on the most important issues in the use of growth factors and stem–cell transplantation?" *J. Clin. Oncol.* (1994) 12:650–652.

Huguet et al., "Differential Expression of Human Wnt Genes 2,3,4 and 7B in Human Breast Cell Lines and Normal and Disease States of Human Breast Tissue" *Cancer Research* (1994) 54:2615–2621.

(List continued on next page.)

*Primary Examiner*—Stephen Walsh
*Assistant Examiner*—Daryl A. Basham
*Attorney, Agent, or Firm*—Morrison & Foerster LLP

[57] ABSTRACT

This invention provides novel human growth factor polypeptides, nucleotides encoding the growth factor polypeptides, and uses for the growth factor polypeptides and polynucleotides.

13 Claims, 2 Drawing Sheets

OTHER PUBLICATIONS

Irvine et al., "fringe, a boundary–specific signaling molecule, mediates interactions between dorsal and ventral cells during Drosophila wing development" *Cell* (1994) 79:595–606.

Kishimoto et al., "Cytokine signal transduction" *Cell* (1994) 76:253–262.

Liesveld et al., "Effect of stem cell factor on myelopoiesis potential in human Dexter–type culture systems" *Exper. Hematol.* (1995) 23:202–209.

Moon, "In pursuit of the functions of the Wnt family of developmental regulators: Insights from *Xenopus laevis*" *BioEssays* (1995) 15:91–97.

Nusse et al., "Many tumors induced by the mouse mammary tumor virus contain a provirus integrated in the same region of the host genome" *Cell* (1982) 31:99–109.

Nusse et al., "A New Nomenclature for int–1 and Related Genes: The Wnt Gene Family" *Cell* (1991) 64:231.

Nusse et al., "Wnt genes" *Cell* (1992) 69:1073–1087.

Parkin et al., "Activity of Wnt–1 as a Transmembrane Protein" *Genes & Development* (1993) 7:2181–2193.

Parr et al., "Wnt genes and vertebrate development" *Current Opinion in Genetics and Development* (1994) 4:523–528.

Sidow, "Diversification of the Wnt gene family on the ancestral lineage of vertebrates" *Proc. Natl. Acad. Sci. USA* (1992) 89:5098–5102.

Slack, "Inducing factors in Xenopus early embryos" *Current Biology* (1994) 4:116–126.

van 't Veer et al., "Molecular cloning and chromosomal assignment of the human homolog of int–1, a mouse gene implicated in mammary tumorigenesis" *Mol. Cell. Biol.* (1984) 4:2532–2534.

Wainwright et al., "Isolation of a human gene with protein sequence similarity to human and murine int–1 and the Drosophila segment polarity mutant wingless" *EMBO J.* (1988) 7:1743–1748.

Williams et al., "Characterization of the gene–product of the steel locus" *Prog. in Growth Factor Res.* (1991) 3:235–242.

Burns in *The Science of Genetics: An Introduction to Heredity* 4ed (1980), Macmillan Publishing Co, Inc, New York p. 220.

Figure 1A

```
                        *         *              *                    *
Consensus         MLEEPRSR.P  P.GLAGLLFL  AL.SRALSNE  ILGLKLPGEP  PLT.NTVCLT

MMU20658 CDS1     MLEEPRSRPP  PLGLAGLLFL  ALFSRALSNE  ILGLKLPGEP  PLTANTVCLT

DV12 cDNA CDS1    MLEEPRSRSP  PSGLAGLLFL  ALCSRALSNE  ILGLKLPGEP  PLTGNTVCLT

*
Consensus         LSGLSKRQLG  LCLR.PDVTA  SALQGLHIAV  HECQHQLRDQ  RWNCSALEGG

MMU20658 CDS1     LSGLSKRQLG  LCLRSPDVTA  SALQGLHIAV  HECQHQLRDQ  RWNCSALEGG

DV12,cDNA CDS1    LSGLSKRQLG  LCLRNPDVTA  SALQGLHIAV  HECQHQLRDQ  RWNCSALEGG

Consensus         GRLPHHSAIL  KRGFRESAFS  FSMLAAGVMH  AVATACSLGK  LVSCGCGWKG

MMU20658 CDS1     GRLPHHSAIL  KRGFRESAFS  FSMLAAGVMH  AVATACSLGK  LVSCGCGWKG

DV12 cDNA CDS1    GRLPHHSAIL  KRGFRESAFS  FSMLAAGVMH  AVATACSLGK  LVSCGCGWKG

*  *  *    *   *
Consensus         SGEQDRLRAK  LLQLQALSRG  K.FP.S.PSP  .PGS.PSPGP  QDTWEWGGCN

MMU20658 CDS1     SGEQDRLRAK  LLQLQALSRG  KIFPISQPSP  VPGSVPSPGP  QDTWEWGGCN

DV12 cDNA CDS1    SGEQDRLRAK  LLQLQALSRG  KSFPHSLPSP  GPGSSPSPGP  ODTWEWGGCN

Consensus         HDMDFGEKFS  RDFLDSREAP  RDIQARMRIH  NNRVGRQVVT  ENLKRKCKCH

MMU20658 CDS1     HDMDFGEKFS  RDFLDSREAP  RDIQARMRIH  NNRVGRQVVT  ENLKRKCKCH

DV12 cDNA CDS1    HDMDFGEKFS  RDFLDSREAP  RDIQARMRIH  NNRVGRQVVT  ENLKRKCKCH

*          *
Consensus         GTSGSCQFKT  CWRAAPEFRA  .GAALRERL.  RAIFIDTHNR  NSGAFQPRLR

MMU20658 CDS1     GTSGSCQFKT  CWRAAPEFRA  IGAALRERLS  RAIFIDTHNR  NSGAFQPRLR

DV12 cDNA CDS1    GTSGSCQFKT  CWRAAPEFRA  VGAALRERLG  RAIFIDTHNR  NSGAFQPRLR
```

Figure 1B

```
                          *
Consensus       PRRLSGELVY FEKSPDFCER DPT.GSPGTR GRACNKTSRL LDGCGSLCCG

MMU20658 CDS1   PRRLSGELVY FEKSPDFCER DPTLGSPGTR GRACNKTSRL LDGCGSLCCG

DV12 cDNA CDS1  PRRLSGELVY FEKSPDFCER DPTMGSPGTR GRACNKTSRL LDGCGSLCCG

Consensus       RGHNVLRQTR VERCHCRFHW CCYVLCDECK VTEWVNVCK

MMU20658 CDS1   RGHNVLRQTR VERCHCRFHW CCYVLCDECK VTEWVNVCK

DV12 cDNA CDS1  RGHNVLRQTR VERCHCRFHW CCYVLCDECK VTEWVNVCK
```

HUMAN GROWTH FACTORS, NUCLEOTIDE SEQUENCE ENCODING GROWTH FACTORS, AND METHOD OF USE THEREOF

TECHNICAL FIELD

This invention relates to growth factors. More specifically, it relates to the polynucleotides encoding a novel human gene (Wnt-10b) and the polypeptides encoded by Wnt-10b.

BACKGROUND

Intercellular signalling proteins are ubiquitous in multicellular organisms. They are involved in the regulation of a number of fundamental biological processes, such as mitosis, protein synthesis, secretion, proliferation, development, metabolism and differentiation. Examples of these signalling proteins include hormones, such as insulin, oncogene products, and growth factors.

Growth factors are also involved in developmental and homeostatic processes. For example, hematopoiesis is the dynamic, complex process of proliferation and differentiation of pluripotent stem cells and progenitor cells into mature blood cells and some specialized tissue cells. Production of functional blood cells is regulated by specific signalling proteins, generically termed hemopoietic growth factors. The range and activities of growth factors vary. Some growth factors control maturation of a specific maturation lineage. Others stimulate proliferation and differentiation of progenitors along multiple pathways. Other growth factors selectively inhibit differentiation. Examples of these signalling molecules are GM-CSF, the Examples of these signalling molecules are GM-CSF, the interleukins, and interferons. Often growth factors have pleiotropic effects whereby a single growth factor will have vastly different effects on different cell types, e.g. on mature cells versus primitive, less differentiated cells, or will differ in expression or effect at different developmental stages.

Many of these growth factors have limited activity alone, and act synergistically with other regulatory molecules to effect essential biological activities. Moreover, many of the genes encoding these growth factors are proto-oncogenes whose inappropriate activation leads to tumorigenesis. In order to understand the roles and possible therapeutic applications of growth factors, it is crucial to identify and characterize these factors.

The ability to initiate and regulate hematopoiesis, and the ability to obtain and sustain hematopoietic cells, especially stem cells, is of increasing and vital importance in medicine. A number of serious diseases, including some malignancies, are caused by a malfunctioning of the hematopoietic system. Because growth factors modulate fundamental cellular processes, they have also found an important use in therapy. For example, cancer therapies can seriously diminish the hematopoietic population, exposing the patient to the danger of opportunistic infection. This danger in turn limits the dose of therapy. By introducing bone marrow cells into the patient, the supply of hematopoietic cells is increased, thus protecting the patient and allowing higher, more effective doses of therapy.

Obtaining viable populations of hematopoietic cells useful in various therapeutic applications requires an ability to maintain and expand stem cell populations.

Stem cells constitute only a small percentage of the total number of hematopoietic cells.

Hematopoietic stem cells give rise to all blood cell types, including all classes of cells in the lymphoid, myeloid, erythroid and megakaryocytic lineages. Stem cells are characterized by their self-regenerative capacity and their ability to differentiate into cells of all hematopoietic lineages. Stem cells find use in: (1) regenerating the hematopoietic system of a host deficient in any class of hematopoietic cells; (2) a host that is diseased and can be treated by removal of bone marrow, isolation of stem cells and treatment with drugs or irradiation prior to re-engraftment of stem cells; (3) producing various hematopoietic cells; (4) detecting and evaluating growth factors relevant to stem cell self-regeneration; and (5) the development of hematopoietic cell lineages and assaying for factors associated with hematopoietic development. Stem cells are important targets for gene therapy, where the inserted genes promote the health of the individual into whom the stem cells are transplanted.

A number of growth factors have been isolated that act on hematopoietic stem cells. The c-kit ligand has been characterized as a stem cell factor. Ksebo et al. (1990) *Cell* 63:195–201 (stem cell factor; SCF); Williams et al. (1990) *Cell* 63:167–174 (mast cell growth factor; MGF); Huang et al. (1990) *Cell* 63:225–233 (c-kit ligand). c-kit ligand is believed to be important in maintaining viability of hematopoietic stem cells in vitro, and synergizes with a number of other growth factors to promote proliferation. Nucleic acids encoding flk-2, a tyrosine kinase receptor expressed in primitive hematopoietic cells, but not mature cells, are described in U.S. Pat. No. 5,270,458. Mouse stem cells have been reported to express receptors for a number of growth factors, including IL-3 and c-mp1 ligand.

Stem cells grow in close contact with bone marrow stromal cells in vivo and in vitro. While not completely understood, stromal cells appear to produce a number of factors regulating stem cell growth and/or differentiation and/or homing. In addition, the role of cell—cell interaction with stromal cells in stem cell regulation is not well understood, although some reports suggest cell adhesion may be required for stem cell self-renewal.

Wnt genes are a group of highly conserved genes central in pattern formation in development and differentiation (for review, see Nusse and Varmus (1992) *Cell* 69:1073–1087). Wnt genes have been found in a wide variety of vertebrates and invertebrates, including human (Van't Veer et al. *Mol. Cell. Biol.* (1984) 4:2532–2534); mouse (Nusse and Varmus (1982) *Cell* 31:99–109); Drosophila (Rijsewijk et al. (1987) *Cell* 50:649–657); and Xenopus (Noordermeer et al. (1989) *Nucl. Acids Res.* 17:11–18). The Wnt gene family encodes highly conserved cysteine-rich glycoproteins. They appear to be secreted but adhere tightly to the plasma membrane and extracellular matrix components, particularly heparin sulfate proteoglycan (HSPG). Smolich et al. (1993) *Mol. Cell. Biol.* 4:1267–1275.

After the discovery of the role of Wnt in Drosophila development, in which a lack of expression was associated with the wingless mutation, much of the interest in Wnt genes has centered on their regulatory role in development. However, Wnt genes have since been found to be expressed in a variety of adult tissues.

Products of Wnt genes are multipotent factors, associated with fundamental developmental phenomena and oncogenic events. As such, they are often associated with extensive cellular proliferation. Patterns of Wnt expression are complex and vary depending on cellular and developmental context.

Because they are ubiquitous and are highly conserved, Wnt gene products probably also modulate a number of other fundamental processes. Recent studies of Wnt-1 indicate that this protein induces mitosis in the developing mammalian central nervous system (CNS). Dickinson et al. (1994) *Development* 120:1453–1471. Members of the Wnt family are expressed in a variety of cell types other than the CNS, indicating that Wnt proteins modulate a variety of fundamental processes in vertebrate embryos. Factors important in pattern formation in development are known to possess pleiotropic activities including regulation of cell growth, survival, and differentiation. Burrus (1994) *BioEssays* 16(3):155–157. Like the FGF and TGF-β family, the Wnt family of molecules is involved both in embryogenesis and oncogenesis.

There remains a need for identification of growth factors involved in regulating hematopoietic cell development. This invention has identified and characterized such proteins.

All publications cited herein are hereby incorporated herein by reference in their entirety.

SUMMARY OF THE INVENTION

The present invention provides polypeptides and polynucleotides encoding the polypeptides for human Wnt-10b and human Wnt-10bΔ.

Accordingly, one aspect of the invention is a non-naturally occurring polynucleotide encoding a human Wnt-10b or Wnt-10bΔ.

Another aspect of the invention is an isolated naturally occurring polynucleotide encoding a human Wnt-10b or Wnt-10bΔ.

In another aspect, the invention includes recombinant polynucleotides having the nucleotide sequence depicted in Seq. I.D. No. 1 or Seq. I.D. No. 3 or a fragment thereof. The invention also includes recombinant polynucleotides having a nucleotide sequence complementary to the sequence(s) depicted in Seq. I.D. No. 1 or Seq. I.D. No. 3 or a fragment thereof.

In another aspect, the invention includes recombinant polynucleotides having a nucleic acid sequence substantially homologous to the nucleic acid sequence depicted in Seq. I.D. No. 1 or Seq. I.D. No. 3 or its complement.

In another aspect, the invention includes recombinant polynucleotides comprising at least about 100 bases of the sequence depicted in Seq. I.D. No. 1 or Seq. I.D. No. 3, provided that these polynucleotides do not consist of a nucleotide sequence identical to mouse Wnt-10b.

In another aspect, the invention includes a polypeptide having the amino acid sequence depicted in Seq. I.D. No. 2 or Seq. I.D. No. 4 or a fragment thereof.

Another aspect of the invention are vectors comprising the polynucleotides of the invention. Also included are host cells comprising the polynucleotides of the invention.

In another aspect, the invention includes a substantially pure naturally occurring polypeptide having the amino acid sequence depicted in Seq. I.D. No. 2 or Seq. I.D. No. 4.

Another aspect of the invention is a non-naturally occurring polypeptide having the amino acid sequence depicted in Seq. I.D. No. 2 or Seq. I.D. No. 4 or a fragment thereof.

Another aspect of the invention is an antibody capable of specifically binding to any of the polypeptides of this invention.

BRIEF DESCRIPTION OF THE DRAWINGS

FIG. 1 compares amino acid sequences of human Wnt-10b (DV12) (Seq. I.D. No. 2) with mouse Wnt-10b (Seq. I.D. No. 6). The consensus sequence is shown at the top of the FIGURE (Seq. I.D. No. 5). Non-identical amino acids are designated by asterisks.

MODES FOR CARRYING OUT THE INVENTION

The growth factor(s) of this invention, designated human Wnt-10b and human Wnt-10bΔ, can be purified from human fetal bone marrow stroma.

The present invention encompasses polynucleotide sequences encoding the human Wnt-10b growth factors, Wnt-10b growth factor polypeptides, and methods of use thereof. The invention further includes vectors having the polynucleotide sequences and recombinant host cells containing polynucleotides that express the growth factor.

Definitions

As used herein, "human Wnt-10b", "human Wnt-10bΔ" and "human Wnt-10b(10b-Δ) polypeptides" refer to proteins or polypeptides encoded by nucleic acid molecules described herein, which in one embodiment can be purified from fetal bone marrow stroma and act on primitive bone marrow cells. A "fragment" of the human Wnt-10b or Wnt-10bΔ polypeptide is a portion of the growth factor and as used herein excludes those fragments which consist of amino acid sequences identical to mouse Wnt-10b protein, as derived from the nucleotide sequence in Genebank (FIG. 1).

The growth factors of this invention are signalling polypeptides that effect various biological activities. These activities include proliferation, differentiation and/or inhibition of differentiation, as well as trophic effects. The human Wnt-10b and Wnt-10bΔ polypeptides of this invention are involved in developmental regulation and act upon bone marrow cells such as stromal cells, hematopoietic stem cells, progenitor cells, and mature cells. Because proteins of the Wnt gene family modulate fundamental cellular functions, the polypeptides of this invention probably act upon other cell types, such as neural cells, primitive, undifferentiated stem cells, and mammary cells.

The term "polynucleotide" refers to a polymeric form of nucleotide of any length, either ribonucleotides, or deoxyribonucleotides, or analogs thereof. This term refers only to the primary structure of the molecule. Thus, this term includes double- and single- stranded DNA and RNA. Polynucleotides encompass RNA, cDNA, genome-derived DNA, synthetic and semi-synthetic forms, mixed polymers, both sense and antisense strands. It also includes known types of modifications, for example labels that are known in the art (e.g., *Molecular Cloning: A Laboratory Manual,* 2nd ed., Vol. 1–3, eds. Sambrook et al. Cold Spring Harbor laboratory Press (1989)), methylation, "caps", substitution of one or more of the naturally occurring nucleotide with an analog, internucleotide modifications such as, for example, those with uncharged linkages (e.g., methyl carbamate, etc.), those containing pendant moieties, such as for example, proteins (including, e.g., nuclease, toxins, antibodies, signal peptides, poly-$_L$ lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. The polynucleotide may be chemically or biochemically modified or contain non-natural or derived nucleotide bases. The nucleotide may be complementary to the mRNA encoding the polypeptides. These complementary nucleotides include, but are not limited to, nucleotides capable of forming triple helices and antisense nucleotides. Recombinant polynucleotides comprising sequences otherwise not naturally occurring are also provided by this invention, as are alterations of wild type polypeptide sequences, including but not limited to, those due to deletion, insertion, substitution of one or more nucleotide or by fusion to other polynucleotide sequences. This definition does not include polynucleotides that consist of a nucleotide sequence identical to mouse Wnt-10b.

As used herein, a "fragment" of a nucleic acid sequence or polynucleotide is a portion of that sequence and has at least 10 nucleotides. "Fragment" does not include polynucleotides consisting of a nucleic acid sequence identical to that of mouse Wnt-10b.

A polynucleotide is said to "encode" a polypeptide if, in its native state or when manipulated by methods well known to those skilled in the art, it can be transcribed and/or translated to produce the polypeptide or mature protein. Thus, the term polynucleotide shall include, in addition to coding sequences, processing sequences and other non-coding sequences which do not code for amino acids of the mature protein. The anti-sense strand of such a polynucleotide is also said to encode the sequence.

The term "recombinant" polynucleotide or DNA refers to a polynucleotide which is made by the combination of two otherwise separated segments of sequence accomplished by the artificial manipulation of isolated segments of DNA by genetic engineering techniques or by chemical synthesis. In so doing one can join together DNA segments of desired functions to generate a desired combination of functions.

As used herein, "naturally occurring," "native," or "wild type" refers to the endogenous human Wnt-10b or Wnt-10bΔ nucleic acids and the Wnt-10b(10bΔ) protein(s) expressed thereby, including alleles and allelic forms of the protein(s). These terms include full-length and processed polynucleotides and polypeptides. Processing can occur in one or more steps, and these terms encompass all stages of processing. For instance, polypeptides having or lacking a signal sequence are encompassed by the invention. "Non-naturally occurring", "non-native", or "non-wild type" refer to all other human Wnt-10b(10bΔ) polynucleotides and polypeptides.

A "signal sequence" is a short amino acid sequence that directs newly synthesized secretory or membrane proteins to and through cellular membranes such as the endoplasmic reticulim. Signal sequences are typically in the N-terminal portion of a polypeptide and are cleaved after the polypeptide has crossed the membrane.

An "isolated" or "substantially pure" polynucleotide is substantially separated from other polynucleotides which naturally accompany a native polynucleotide sequence. The term particularly refers to genomic DNA isolated from other, native DNA sequences. The term embraces a polynucleotide sequence which has been removed from its naturally occurring environment, and includes recombinant or cloned DNA isolates and chemically synthesized analogues or analogues biologically synthesized by heterologous systems. The terms "substantially pure" or "isolated" are not intended to exclude mixtures of polynucleotides or polypeptides with substances that are not associated with the polynucleotides or polypeptides in nature.

A polynucleotide or fragment thereof is "substantially homologous" (or "substantially similar") to another if, when optimally aligned (with appropriate nucleotide insertions or deletions) with another polynucleotide (or its complementary strand), there is nucleotide sequence identity in at least about 70% of the nucleotide bases, usually at least about 80%, preferably at least about 90%, and more preferably at least about 95 to 98% of the nucleotide bases. Excluded from the definition of "substantially homologous" or "substantially similar" are polynucleotides consisting of a nucleotide sequence identical to mouse Wnt-10b.

A "vector" is a self-replicating nucleic acid molecule that transfers an inserted nucleic acid molecule into and/or between host cells. The term includes vectors that function primarily for insertion of a nucleic acid molecule into a cell, replication vectors that function primarily for the replication of nucleic acid, and expression vectors that function for transcription and/or translation of the DNA or RNA. Also included are vectors that provide more than one of the above functions.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic or total DNA complement) to the original parent cell due to natural, accidental, or deliberate mutation. "Host cell" indicates that the nucleic acid molecule of interest is exogenous, and the definition does not include those cells which contain the Wnt-10b and/or Wnt-10bΔ gene(s) endogenously.

"Expression systems" are defined as polynucleotides which, when introduced into an appropriate host cell, can be transcribed and translated into a polypeptide(s).

As used herein, the term "polypeptide" refers to a polymer of amino acids and does not refer to a specific length of the product; thus, peptides, oligopeptides, and proteins are included within the definition of polypeptide. This term includes post-expression modifications of the polypeptide, for example, glycosylations, acetylations, phosphorylations, post-translation cleavage(s) and the like. Included within the definition are, for example, polypeptides containing one or more analogs of an amino acid (including, for example, unnatural amino acids, etc.), polypeptides with substituted linkages, as well as other modifications known in the art, such as fusions, both naturally occurring and non-naturally occurring.

A "fragment" of a polypeptide is a portion of any of the above polypeptides, and excludes fragments which consist of an amino acid sequence identical to mouse Wnt-10b protein. A "functional fragment" of the human Wnt-10b or human Wnt-10bΔ growth factor is a portion of the growth factor that exhibits at least one biological activity of naturally-occurring growth factor, and excludes those fragments which consist of an amino acid sequence identical to mouse Wnt-10b protein. As used herein, a "fragment" or a "functional fragment" of a polypeptide is at least five amino acids in length.

The term "purified" or "substantially purified" polypeptide or "isolated" polypeptide refers to a polypeptide or fragment thereof which is essentially free of cellular components with which the polypeptide is naturally associated. Techniques for purifying polypeptides are known in the art.

As used herein, an "antibody" means a protein that is produced in response to exposure to an antigen and that reacts with the antigen with an effective specificity and affinity for its intended purpose. Exposure to an antigen includes immunization. The term "antibody" includes fragments of these antibodies, e.g., Fab, Fab', $F(ab')_2$, $F_v$, single-chain mutants, fusion proteins, humanized proteins, and modifications that comprise an antigen recognition site.

Antibodies include, but are not limited to, mouse, rat, rabbit or human antibodies. "Antibody" also generically includes polyclonal antibodies and monoclonal antibodies. The term "monoclonal antibody" means an immunoglobulin derived from a single clone of cells.

An antibody "specifically binds" to a polypeptide if it binds with greater affinity or avidity than it binds to other polypeptides or substances.

Polynucleotides

The present invention encompasses polynucleotide sequences encoding human Wnt-10b, human Wnt-10bΔ, and fragments thereof. Unless specifically stated otherwise, the terms "polynucleotides", "Wnt-10b polynucleotide(s)", "Wnt-10bΔ polynucleotide(s)", or "Wnt-10b(Δ) polynucleotides" shall include all embodiments of the polynucleotides of this invention. In all instances, the polynucleotides include human sequences as well as allelic forms of the Wnt-10b and Wnt-10bΔ gene(s).

The Wnt-10b growth factors of this invention regulate growth and differentiation of embryonic and bone marrow cells, and are expressed in fetal bone marrow stroma. They are likely expressed in other tissue types, e.g., the central nervous system.

In one embodiment of this invention, the polynucleotide is a non-naturally occurring polynucleotide encoding human Wnt-10b or human Wnt-10bΔ. In another embodiment, the polynucleotide is an isolated naturally occurring polynucleotide encoding human Wnt-10b or human Wnt-10bΔ.

In another embodiment of this invention, the polynucleotide is a cDNA encoding either of the growth factors shown in Seq. I.D. No. 2 or Seq. I.D. No. 4 or a fragment thereof. Seq. I.D. No. 2 shows the amino acid sequence of human Wnt-10b (DV12). A Wnt-10b variant, Wnt-10bΔ, is shown in Seq. I.D. No. 4 (DV12/17). The nucleotide sequences of the Wnt-10b and Wnt-10bΔ cDNAs have been compared with the nucleotide sequences recorded in Genebank. These sequences exhibit homology to mouse Wnt-10b, a member of the Wnt gene family. (See Sidow, *Proc. Nat. Acad. Sci. USA* (1992) 89:5098–5102, for amino acid sequences of various Wnt family members.) In a separate embodiment, the polynucleotide is a nucleic acid molecule coding for the amino acid sequence of the native human Wnt-10b or Wnt-10bΔ growth factor(s) or either of the amino acid sequences shown in Seq. I.D. No. 2 or Seq. I.D. No. 4.

In one embodiment, the polynucleotide(s) is recombinant and has the nucleotide sequence depicted in either Seq. I.D. No. 1 or Seq. I.D. No. 3 or a fragment thereof. In another embodiment, the polynucleotide(s) is recombinant and is complementary to the nucleotide sequence depicted in either Seq. I.D. No. 1 or Seq. I.D. No. 3 or a fragment thereof. Seq. I.D. No. 1 depicts the nucleotide sequence and derived amino acid sequence of a human Wnt-10b growth factor. The polynucleotide sequence of Seq. I.D. No. 1 is 2122 base pairs and was derived from clone DV12, as described in Example 1. The nucleotide sequence of Seq. I.D. No. 1 contains a 5' noncoding sequence of 193 base pairs and a 3' noncoding sequence of 762 base pairs. The nucleotide sequence of Seq. I.D. No. 1 encodes a Wnt-10b polypeptide of 389 amino acids, which is also shown in Seq. I.D. No. 2. Seq. I.D. No. 3 is the polynucleotide sequence and derived amino acid sequence of another human Wnt-10b growth factor, Wnt-10bΔ. The nucleotide sequence of Seq. I.D. No. 3 is 1748 base pairs and was derived from clone DV12/17, which is described in Example 1. The nucleotide sequence of Seq. I.D. No. 3 contains a 5' noncoding sequence of 193 base pairs and a 3' noncoding sequence of 1170 base pairs.

The nucleotide sequence of Seq. I.D. No. 3 encodes a human Wnt-10bΔ growth factor of 115 amino acids, which are also shown in Seq. I.D. No. 4. The amino acid sequence of Wnt-10b and Wnt-10bΔ are identical except that Wnt-10bΔ lacks the amino acid sequence from amino acid 114 to amino acid 389 of Wnt-10b. The difference appears to arise from a deletion that changes the reading frame, causing termination of the Wnt-10bΔ protein within three amino acids after the deletion.

The DV12 and DV12/17 plasmids containing cloned Wnt-10b and Wnt-10bΔ cDNAs, respectively, have been deposited with the American Type Culture Collection (ATCC), 12301 Parklawn Drive, Rockville, Md., U.S.A. 20852 on Jun. 8, 1995 under the provisions of the Budapest Treaty for the International Recognition of the Deposit of Microorganisms for the Purposes of Patent Procedure. They were accorded Accession Nos. 97208 and 97207.

The invention includes modifications to the growth factor polynucleotides described above such as deletions, substitutions and additions, particularly in the non-coding regions of genomic DNA. A "modification" is any difference in nucleotide sequence, as compared to a polynucleotide of this invention such as the native polynucleotide sequences. Such changes are useful to facilitate cloning and modifying gene expression. It should be understood, although not always expressed herein, that these modifications do not include nucleotide sequences that consist of nucleotide sequences identical to mouse Wnt-10b gene.

The invention encompasses growth factor polynucleotides including full-length (unprocessed), processed, coding, non-coding or portions thereof. The polynucleotides also are complementary to the mRNA for at least a fragment of the Wnt-10b(Δ) growth factor gene(s) and other polynucleotides which can bind to either the DNA or mRNA encoding the growth factor.

The invention encompasses polynucleotides coding for functionally equivalent variants and derivatives of Wnt-10b or Wnt-10bΔ which may enhance, decrease or not significantly affect properties of the polypeptides encoded thereby. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties. All above-described polynucleotides encoding functionally equivalent variants are included in this invention except for polynucleotides consisting of a sequence identical to mouse Wnt-10b protein.

For example, various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems. These substitutions can be readily obtained by one skilled in the art.

The invention also includes polynucleotide sequences encoding Wnt-10b or Wnt-10bΔ variants including, e.g., other alternatively processed sequences or sequences encoding fusion and deletion proteins. Alternatively processed polynucleotide sequence variants are defined as polynucleotide sequences corresponding to mRNAs that differ in sequence from one another but are derived from the same genomic region, for example, mRNAs that result from: 1) the use of alternative promoters; 2) the use of alternative polyadenylation sites; or 3) the use of alternative splice sites.

The invention further encompasses recombinant polynucleotide sequences which encode the amino acid sequence (s) depicted in Seq. I.D. No. 2 or Seq. I.D. No. 4 or a fragment thereof. The polynucleotide sequence may be similar to those depicted in Seq. I.D. No. 2 or Seq. I.D. No. 4 with minor changes designed to optimize codon usage or stability or may vary significantly, as long as the polynucleotide does not consist of a nucleic acid sequence identical to mouse Wnt-10b. It is within the skill of one in the art, given the amino acid sequence in Seq. I.D. No. 2 or Seq. I.D. No. 4 to design such polynucleotides.

The invention also includes polynucleotide sequences which encode fragments of the amino acid sequence depicted in Seq. I.D. No. 2 or Seq. I.D. No. 4, provided that these polynucleotides do not consist of a nucleic acid sequence identical to mouse Wnt-10b or do not encode for an amino acid sequence identical to the mouse Wnt-10b protein.

The invention also encompasses polynucleotides substantially homologous to the nucleotide sequence depicted in Seq. I.D. No. 1 or Seq. I.D. No. 3, complementary sequences thereto, or a fragment thereof. One indication of substantial homology (or similarity) is if a polynucleotide or fragment thereof will hybridize to another polynucleotide (or a complementary strand thereof) under selective hybridization conditions. Selectivity of hybridization exists under hybridization conditions which allow one to distinguish the target polynucleotide of interest from other polynucleotides. Typically, selective hybridization will occur when there is at least about 55% similarity over a stretch of at least about 14 nucleotides, preferably at least about 65%, more preferably at least about 75%, and most preferably at least about 90%. Kanehisa (1984) *Nuc. Acids Res.* 12:203–213. The length of homology comparison, as described, may be over longer stretches, and in certain embodiments will often be over a stretch of at least 17 to 20 nucleotides, and preferably at least about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1M, typically less than 500 mM, and preferably less than 200 mM. However, the combination of parameters is much more important than the measure of any single parameter. Wetmur and Davidson (1968) *J. Mol. Biol.* 31:349–370.

Also provided by this invention are polynucleotides covalently linked with a detectable label. Such polynucleotides are useful, for example, as probes for detection of related nucleotide sequences.

Techniques for nucleic acid manipulation useful for the practice of the present invention are described in a variety of references, including but not limited to, *Molecular Cloning: A Laboratory Manual,* 2nd ed., Vol. 1–3, eds. Sambrook et al. Cold Spring Harbor Laboratory Press (1989); and *Current Protocols in Molecular Biology*, eds. Ausubel et al., Greene Publishing and Wiley-Interscience: New York (1987) and periodic updates.

The polynucleotides of this invention are useful in expression systems for the recombinant production of human Wnt-10b and Wnt-10bΔ polypeptides and proteins. They are also useful as hybridization probes to assay for expression of the gene(s) in a sample using methods well known to those of skill in the art.

The polynucleotides of this invention can be obtained using recombinant methods, chemical synthesis, or PCR. Recombinant methods employ the vectors and expression systems described below and are described in Example 1. Methods of chemical polynucleotide synthesis are well known in the art and need not be described in detail herein. One of skill in the art can use the sequences provided herein and a commercial DNA synthesizer to replicate the DNA. Alternatively, one of skill in the art can insert the nucleic acid into a suitable vector and insert the vector into a suitable host cell for replication and amplification. The DNA so amplified can be isolated from the cell by methods well known to those of skill in the art.

Alternatively, PCR allows reproduction of DNA sequences. PCR technology is the subject matter of U.S. Pat. Nos. 4,683,195, 4,800,159, 4,754,065 and 4,683,202 and is described in *PCR: The Polymerase Chain Reaction* Mullis et al. eds. Birkauser Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, for example, as set forth in Sambrook et al. (1989) supra.

The polynucleotides of the invention include polynucleotides encoding fragments of the growth factor, except for polynucleotides which consist of nucleotide sequences identical to mouse Wnt-10b. The polynucleotide fragments that are useful, for example, as probes, substrate, therapeutic agents, and as a template for encoding various functional and/or binding domains of the growth factor. In one embodiment, the polynucleotide fragments comprise at least about 45 bases of the sequence depicted in Seq. I.D. No. 1 or Seq. I.D. No. 3, provided that the polynucleotide does not consist of a nucleotide sequence identical to mouse Wnt10-b. A fragment of this approximate size could encode for a functional domain, or a binding site for an antibody. Alternatively, these fragments can serve as probes. Suitable fragments are those which hybridize specifically to growth factor DNA or RNA such that they are effective as primers or probes. The primers are particularly useful in the polymerase chain reaction (PCR).

Polynucleotides encoding functional (bioactive) fragments of a human Wnt-10b (Wnt-10bΔ) growth factor can be obtained by generating polynucleotide fragments and testing the resultant polypeptides for the bioactivity of interest. For example, polypeptides can be tested for their ability to promote cell proliferation (or other suitable biological activity) by contacting the cells with the polypeptide to be tested.

The polynucleotide fragments described above can be generated chemically or enzymatically using techniques well known in the art, as discussed above.

The polynucleotides of this invention also are useful to obtain homologous DNA sequences encoding other closely related Wnt-10b genes, such as alleles of the Wnt-10b gene. Methods for constructing appropriate cDNA and genomic libraries, for screening libraries for sequences of interest, for preparing suitable probes or primers (e.g., PCR primers), for polynucleotide purification, amplification and subcloning, and for host cell transformation and other techniques of recombinant DNA technology appropriate to the practice of the present invention are provided, inter alia, in Sambrook, et al., (1989); Ausubel et al. (1987 and periodic updates); and *PCR Protocols: A Guide to Methods and Applications*, Innis et al., eds., Academic Press: San Diego (1990). Reagents useful in applying such techniques, such as restriction enzymes, expression vectors, labels, etc. are known in the art and commercially available from such vendors as New England BioLabs, Boehringer Mannheim, Amersham, Promega Biotec, U.S. Biochemicals, New England Nuclear, and a number of other commercial sources.

The invention further includes a variety of vectors having cloned therein the polynucleotide sequence(s) described above. These vectors can be used for expression of recombinant polypeptides, as well as a source of the polynucleotides. Suitable vectors include any known in the art, e.g., those for use in bacterial, mammalian, yeast and insect expression systems. Specific vectors and suitable host cells are known in the art and need not be described in detail herein. See, for example, Gacesa and Ramji, *Vectors* John Wiley & Sons (1994).

Another embodiment of this invention are host cells transformed with vectors having the polynucleotide sequences described above. Both prokaryotic and eukaryotic host cells may be used. Prokaryotic hosts include *E. coli*. Among eukaryotic hosts are yeast, insect, and mammalian cells. Host systems are known in the art and need not be described in detail herein.

Expression systems prepared for introduction into a prokaryotic or eukaryotic host will typically comprise a replication system recognized by the host, including the intended DNA fragment encoding the desired polypeptide (s), and will preferably also include transcription and translational initiation regulatory sequences operably linked to the polypeptide encoding segment. Expression systems (expression vectors) may include, for example, an origin or replication or autonomously replicating sequence (ARS) and expression control sequence, a promoter, an enhancer and necessary processing information sites, such as ribosome-binding sites, RNA splice sites, polyadenylation sites, transcriptional terminator sequences, and mRNA stabilizing sequences. DNA encoding signal peptides may also be included which allow the polypeptide of the invention to cross and/or lodge in cell membranes or be secreted from the cell.

The selection of an appropriate promoter and other necessary vector sequences will be selected so as to be functional in the host. Examples of workable combinations of cell lines and expression vectors are described in Sambrook et al., 1989; Ausubel et al., 1987; and Metzger et al., *Nature* 334:31, 1988. In addition, the construct may be joined to an amplifiable gene (e.g., DHFR) so that multiple copies of the gene may be made. For appropriate enhancer and other expression control sequences see also *Enhancers and Eukaryotic Gene Expression*, Cold Spring Harbor Press, N.Y. (1983). While such expression vectors may replicate autonomously, they may less preferably replicate by being inserted into the genome of the host cell.

Further, the invention encompasses cells transfected in vivo by the vectors. Suitable methods of in vivo transfection are known in the art and include, but are not limited to, that described by Zhu et al. (1993) *Science* 261:209–211.

Expression and cloning vectors can contain a selectable marker, a gene encoding a protein necessary for the survival or growth of a host cell transformed with the vector, although such a selectable gene can be carried on another polynucleotide sequence co-introduced into the host cell. Only those host cells into which the selectable gene has been introduced will survive and/or grow under selective conditions. Typical selection genes encode protein(s) that (a) confer resistance to antibiotics or other toxic substances, e.g. ampicillin, neomycin, methotrexate, etc.; (b) complement auxotrophic deficiencies, or (c) supply critical nutrients not available from complex media. The choice of the proper selectable gene will depend on the host cell, and appropriate genes for different hosts are known in the art.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; infection (where the vector is an infectious agent, such as a retroviral genome). The choice of such means will often depend on the host cell.

Also encompassed by this invention are plasmids comprising polynucleotides encoding Wnt-10b as deposited in ATCC Accession No. 97208. The invention also includes plasmids comprising polynucleotides encoding Wnt-10bΔ as deposited in ATCC Accession No. 97207. Vector (plasmid) DV12 contains the nucleotide sequence encoding human Wnt-10b. Vector (plasmid) DV12/17 contains the nucleotide sequence encoding Wnt-10bΔ. These polynucleotides (or fragments thereof) can be obtained by methods well known in the art. Host cells containing the vector(s) are grown under suitable conditions and the vector DNA is isolated using standard methods. Once isolated, the desired polynucleotide is obtained by an appropriate restriction enzyme digest of the isolated DNA to liberate the desired polynucleotide from the vector. A suitable separation technique such as gel electrophoresis can be used to isolate the polynucleotide from the other restriction fragments. Location of restriction sites is readily possible using sequence analysis.

Transgenic animals containing the recombinant polynucleotides or vectors are also encompassed by the invention. Methods of making transgenic animals are known in the art and need not be described in detail herein. See, e.g., PCT publication WO 93/04169. Preferably, such animals express a recombinant growth factor polynucleotide under control of a cell-specific promoter.

The invention also encompasses compositions having any of the polynucleotides described above and a suitable solid or liquid. These compositions include, but are not limited to, polynucleotide(s) in a hybridization mixture, polynucleotide(s) in a physiologically acceptable buffer, and polynucleotides attached to a solid or semi-solid substrate. These compositions may be used for a variety of applications, including, but not limited to, hybridization, in vivo and ex vivo transfection and in vitro transfection.

Polypeptides

The invention also provides a human Wnt-10b and human Wnt-10bΔ growth factor polypeptide(s) and fragments thereof. The human Wnt-10b (Wnt-10bΔ) polypeptides of the present invention have pleiotropic activities, including activities regulating embryonic development and regulating growth and/or differentiation of bone marrow cells. The Wnt-10b (Wnt-10bΔ) polypeptides can also be used to identify its receptor from responsive cells and for the production of specific antibodies.

Unless specifically stated, the term "polypeptides" shall include all embodiments of the polypeptides of this invention.

In one embodiment, a polypeptide of this invention is an isolated polypeptide encoded by any of the polypeptides described above. These polypeptides can be obtained from a variety of expression systems. This in turn can result in polypeptides that differ in terms of processing, including, but not limited to, glycosylation differences or absence.

In another embodiment, a polypeptide of this invention has either of the amino acid sequences shown in Seq. I.D. No. 2 or Seq. I.D. No. 4. In one embodiment, a substantially pure naturally occurring polypeptide has an amino acid sequence shown in Seq. I.D. No. 2 or has an amino acid sequence from about amino acid 22 to amino acid 389 depicted in Seq. I.D. No. 2. In another embodiment, a substantially pure naturally occurring polypeptide has an amino acid sequence depicted in Seq. I.D. 4 or has an amino acid sequence from about amino acid 22 to amino acid 115 depicted in Seq. I.D. No. 4. The sequences of amino acid about 22 to 389 in Seq. I.D. No. 2 and amino acid about 22 to 115 in Seq. I.D. No. 4 are meant to encompass Wnt-10b- and Wnt-10bΔ polypeptides that lack a signal sequence.

In another embodiment, the polypeptides of this invention are non-naturally occurring and have an amino acid sequence depicted in Seq. I.D. No. 2 or Seq. I.D. No. 4 or a fragment thereof. Human Wnt-10b and human Wnt-10bΔ growth factor polypeptides encompass fragments of the growth factor(s), as long as these fragments do not consist of an amino acid sequence identical to mouse Wnt-10b. Such fragments can have at least one of the biological activities discussed above. However, useful polypeptide fragments of this invention need not have any of the above biological activities. For instance, a polypeptide fragment can be used to elicit an immune response. Alternatively, a growth factor polypeptide fragment can be used to assay for other growth factor antagonism or synergy.

The invention includes modifications to the polypeptide sequence including functionally equivalent variants of the polypeptides which do not significantly affect their properties and variants which retain the overall amino acid sequence but which have enhanced or decreased activity. These modifications exclude those polypeptides consisting of an amino acid sequence identical to mouse Wnt-10b protein. Such polypeptides include polypeptides with conservative substitutions of amino acid residues, or one or a few deletions or additions of amino acids which do not change the functional activity. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. These polypeptides also include glycosylated and nonglycosylated polypeptides, as well as polypeptides with other post-translational changes, such as glycosylation with different sugars, acetylation, etc. Preferably, the amino acid substitutions would be conservative, i.e., the substituted amino acid would possess similar chemical properties as that of the original amino acid. Such conservative substitutions are known in the art.

Polypeptides thus obtained can be tested for their ability to promote cell proliferation (or other suitable biological activity) by contacting the cells with the polypeptide to be tested.

Representative polypeptides of this invention, include, but are not limited to, amino acids 7 to 14, amino acids 7 to 25, and amino acids 7 to 46 of the amino acid sequence depicted in Seq. I.D. No. 2 or Seq. I.D. No. 4; and amino acids 169 to 189 and amino acids 169 to 187 of the amino acid sequence depicted in Seq. I.D. No. 2.

The polypeptides of this invention can be made by procedures known in the art. The polypeptides can be produced by proteolytic or other degradation of a growth factor polypeptide, by recombinant methods (i.e., single or fusion polypeptides) as described above or by chemical synthesis. Preferably, the polypeptides are at least partially purified from other cellular constituents. Preferably, the proteins are at least 50% pure. More preferably, the proteins are 50–75% pure. More highly purified polypeptides may also be obtained and are encompassed by the present invention. For clinical use, the polypeptides are preferably highly purified, at least about eighty percent pure, and free of pyrogens and other contaminants. Methods of protein purification are known in the art and are not described in detail herein. Techniques for expressing the polypeptides alone or as fusion proteins are also known in the art. Purification or isolation of the polypeptides expressed in host systems can be accomplished by any method known in the art.

Suitable methods of protein purification are known in the art and include, but are not limited to, affinity chromatography, immunoaffinity chromatography, size exclusion chromatography, HPLC and FPLC. Any purification scheme that does not result in substantial degradation of the polypeptide is suitable for use in the present invention.

The invention also includes substantially purified naturally occurring growth factor having the amino acid sequence depicted in Seq. I.D. No. 2 or Seq. I.D. No. 4. The invention encompasses functionally equivalent variants of the growth factor which do not significantly affect its properties and variants which retain the same overall amino acid sequence but which have enhanced or decreased activity. For instance, conservative substitutions of amino acid residues, one or a few amino acid deletions or additions, and substitution of amino acid residues by amino acid analogs are within the scope of the invention. Conservative amino acid substitution has been discussed above.

The invention also encompasses compositions having any of the polypeptides described above and a suitable solid or liquid, e.g., culture media. These compositions are useful for, e.g., ex vivo manipulation of bone marrow cells and embryonic cells. These compositions include pharmaceutical compositions.

Antibodies

Also provided by this invention is an antibody capable of specifically binding with the human Wnt-10b (10bΔ) polypeptide(s) and fragments thereof as described above.

Laboratory methods for producing polyclonal antibodies are known in the art, such as Harlow and Lane, *Antibodies: A Laboratory Manual*, Cold Spring Harbor Laboratory, New York (1988) and Sambrook et al. (1989) supra. The monoclonal antibodies of this invention can be biologically produced by introducing the Wnt-10b(10bΔ) polypeptide or a fragment thereof into an animal, e.g., a mouse or a rabbit. The antibody-producing cells in the animal are isolated and fused with myeloma cells or heteromyeloma cells to produce hybrid cells or hybridomas. Accordingly, the hybridoma cells producing the monoclonal antibodies of this invention also are provided. Using the Wnt-10b(10bΔ) polypeptide(s) described herein, and well known methods, one of skill in the art can produce and screen the hybridoma cells and antibodies of this invention for antibodies having the ability to specifically bind the Wnt-10b polypeptide.

The invention also encompasses uses of the human Wnt-10b(10bΔ) polypeptides or polynucleotides encoding the Wnt-10b(10bΔ) polypeptides. For example, the polynucleotides of the present invention may be introduced and expressed in primary or cloned stromal cell lines. Such cell lines expressing the Wnt-10b (10bΔ) protein(s) can then be used in the ex vivo culture of human hematopoietic stem cells to promote proliferation and/or differentiation. Alternatively, purified Wnt-10b(10bΔ) polypeptides may be added to ex vivo cultures of bone marrow cells, alone or in combination with other growth factors, in amounts effective to act on stromal and/or hematopoietic cells to regulate cell growth. If purified Wnt-10b(10bΔ) protein(s) is used in the ex vivo culture of hematopoietic cells in the absence of stromal cells, extracellular matrix components, particularly heparin sulfate proteoglycan (HSPG), should be included in the culture to aid presentation of the ligand to the responsive cells.

As is apparent to those of skill in the art, any of the polynucleotides, polypeptides, proteins, vectors, host cells, antibodies, or antibody fragments can be used for the preparation of a medicament for the prevention and/or treatment of pathologies associated with either over-expression or under-expression of Wnt-10b(10bΔ) growth factor protein(s).

The following examples are provided to illustrate but not limit the present invention.

EXAMPLE 1

Cloning Human Wnt-10b and Human Wnt-10bΔ cDNA

Unless otherwise specified, all cloning techniques were essentially as described by Sambrook et al. (1989) and all reagents were used according to the manufacturer's instructions.

Fetal bone marrow stromal cells were isolated from a 20 week fetus obtained by informed consent by fragmenting quartered bones and culturing the bone chips in Whitlock/Witte media (1:1 IMDM:RPMI with 10 fetal calf serum, 1 mM sodium pyruvate, penicillin/streptomycin, and glutamine). Media was changed every other day. After approximately 14 days, total RNA was isolated from the adherent cells using RNA STAT-60 (Tel-Test"B"; Austin, Tex.) according to the manufacturer's instructions. 1 μg of the total RNA was reverse-transcribed using Moloney Murine Leukemia virus reverse transcriptase and a random oligomer for priming. $\frac{1}{20}$th of the cDNA was used in a PCR reaction containing consensus primers to conserved amino acid sequences within the Wnt gene family.

The product from the reaction having approximately the correct size was subcloned into a TA cloning vector pGEM-T (Promega). Independent clones were sequenced, revealing the identification of DV12, having homology to the Wnt gene family, within the fetal bone marrow stromal cell RNA.

cDNA clones were isolated as follows. Total RNA was isolated from a second fetal culture set up as described above (from cells cultured for approximately 18 days) using RNA STAT-60. Approximately 700 μg of total RNA was used to isolate mRNA by an oligo-dT cellulose column (Pharmacia). Recovery of mRNA was estimated to be 10 μg. The isolated mRNA was divided in half and used to generate an oligo-dT primed and a random-primed cDNA library using a Lambda-ZAP Express cDNA kit (Stratagene). cDNA was size-fractionated using Sephacryl S-500HR (Life Technologies). Fractions containing the first peak and two subsequent fractions were collected for library construction.

A total of $1\times10^6$ independent clones were isolated from the oligo-dT primed library and screened in pools of 50,000 by PCR using primers specific to each of the Wnt gene family. Positive phage pools were plated and plaque lifts from size plates containing approximately 120,000 clones were prepared for screening.

The original PCR insert was labeled with $^{32}P$ and used to probe the resulting filters. Duplicate signals indicated positive primary phage clones. The positives were picked and replated at low density to obtain single plaques. Filter lifts were prepared and hybridized with the corresponding probe. Three independent phage plaques were isolated and subjected to plasmid excision following a protocol by Stratagene.

Plasmid DNA was prepared from each clone and subjected to DNA sequencing using T7 and T3 primers contained within the cDNA vector and specific primers identical to the PCR primers used to identify the positive phage pools. Full length cDNA sequence was obtained by primer walking on both strands of the cDNA. cDNA and derived amino acid sequence for Wnt-10b is shown in Seq. I.D.No. 1. cDNA and derived amino acid sequence for Wnt-10bΔ is shown in Seq. I.D. No. 3.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2122 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 194..1360

( x i ) SEQUENCE DESCRIPTION: SEQ ID NO:1:

```
GAAGCGGTGA AGAGGAGTGG CCCGGCCCTG GAAGAATGCG GCTCTGACAA GGGGACAGAA        60

CCCAGCGCAG TCTCCCCACG GTTTAAGCAG CACTAGTGAA GCCCAGGCAA CCCAACCGTG       120

CCTGTCTCGG ACCCCGCACC CAAACCACTG GAGGTCCTGA TCGATCTGCC CACCGGAGCC       180

TCCGGGCTTC GAC ATG CTG GAG GAG CCC CGG TCG CGG TCT CCG CCC TCG         229
            Met Leu Glu Glu Pro Arg Ser Arg Ser Pro Pro Ser
              1               5                        10

GGC CTC GCG GGT CTC CTG TTC CTG GCG TTG TGC AGT CGG GCT CTA AGC        277
Gly Leu Ala Gly Leu Leu Phe Leu Ala Leu Cys Ser Arg Ala Leu Ser
         15                  20                  25

AAT GAG ATT CTG GGC CTG AAG TTG CCT GGC GAG CCG CCG CTG ACG GGC        325
Asn Glu Ile Leu Gly Leu Lys Leu Pro Gly Glu Pro Pro Leu Thr Gly
     30                  35                  40

AAC ACC GTG TGC TTG ACG CTG TCC GGC CTG AGC AAG CGG CAG CTA GGC        373
Asn Thr Val Cys Leu Thr Leu Ser Gly Leu Ser Lys Arg Gln Leu Gly
 45                  50                  55                  60

CTG TGC CTG CGC AAC CCC GAC GTG ACG GCG TCC GCG CTT CAG GGT CTG        421
Leu Cys Leu Arg Asn Pro Asp Val Thr Ala Ser Ala Leu Gln Gly Leu
                 65                  70                  75

CAC ATC GCG GTC CAC GAG TGT CAG CAC CAG CTG CGC GAC CAG CGC TGG        469
His Ile Ala Val His Glu Cys Gln His Gln Leu Arg Asp Gln Arg Trp
             80                  85                  90

AAC TGC TCC GCG CTT GAG GGC GGC GGC CGC CTG CCG CAC CAC AGC GCC        517
Asn Cys Ser Ala Leu Glu Gly Gly Gly Arg Leu Pro His His Ser Ala
         95                 100                 105

ATC CTC AAG CGC GGT TTC CGA GAA AGT GCT TTT TCC TTC TCC ATG CTG        565
Ile Leu Lys Arg Gly Phe Arg Glu Ser Ala Phe Ser Phe Ser Met Leu
     110                 115                 120

GCT GCT GGG GTC ATG CAC GCA GTA GCC ACG GCC TGC AGC CTG GGC AAG        613
Ala Ala Gly Val Met His Ala Val Ala Thr Ala Cys Ser Leu Gly Lys
125                 130                 135                 140

CTG GTG AGC TGT GGC TGT GGC TGG AAG GGC AGT GGT GAG CAG GAT CGG        661
Leu Val Ser Cys Gly Cys Gly Trp Lys Gly Ser Gly Glu Gln Asp Arg
                 145                 150                 155

CTG AGG GCC AAA CTG CTG CAG CTG CAG GCA CTG TCC CGA GGC AAG AGT        709
Leu Arg Ala Lys Leu Leu Gln Leu Gln Ala Leu Ser Arg Gly Lys Ser
             160                 165                 170

TTC CCC CAC TCT CTG CCC AGC CCT GGC CCT GGC TCA AGC CCC AGC CCT        757
Phe Pro His Ser Leu Pro Ser Pro Gly Pro Gly Ser Ser Pro Ser Pro
         175                 180                 185

GGC CCC CAG GAC ACA TGG GAA TGG GGT GGC TGT AAC CAT GAC ATG GAC        805
Gly Pro Gln Asp Thr Trp Glu Trp Gly Gly Cys Asn His Asp Met Asp
     190                 195                 200

TTT GGA GAG AAG TTC TCT CGG GAT TTC TTG GAT TCC AGG GAA GCT CCC        853
Phe Gly Glu Lys Phe Ser Arg Asp Phe Leu Asp Ser Arg Glu Ala Pro
205                 210                 215                 220

CGG GAC ATC CAG GCA CGA ATG CGA ATC CAC AAC AAC AGG GTG GGG CGC        901
Arg Asp Ile Gln Ala Arg Met Arg Ile His Asn Asn Arg Val Gly Arg
                 225                 230                 235

CAG GTG GTA ACT GAA AAC CTG AAG CGG AAA TGC AAG TGT CAT GGC ACA        949
Gln Val Val Thr Glu Asn Leu Lys Arg Lys Cys Lys Cys His Gly Thr
             240                 245                 250

TCA GGC AGC TGC CAG TTC AAG ACA TGC TGG AGG GCG GCC CCA GAG TTC        997
Ser Gly Ser Cys Gln Phe Lys Thr Cys Trp Arg Ala Ala Pro Glu Phe
         255                 260                 265

CGG GCA GTG GGG GCG GCG TTG AGG GAA CGG CTG GGC CGG GCC ATC TTC       1045
Arg Ala Val Gly Ala Ala Leu Arg Glu Arg Leu Gly Arg Ala Ile Phe
     270                 275                 280
```

| | | | | | | | | | | | | | | | | |
|---|---|---|---|---|---|---|---|---|---|---|---|---|---|---|---|---|
| ATT | GAT | ACC | CAC | AAC | CGC | AAT | TCT | GGA | GCC | TTC | CAG | CCC | CGT | CTG | CGT | 1093 |
| Ile | Asp | Thr | His | Asn | Arg | Asn | Ser | Gly | Ala | Phe | Gln | Pro | Arg | Leu | Arg | |
| 285 | | | | 290 | | | | | 295 | | | | | | 300 | |
| CCC | CGT | CGC | CTC | TCA | GGA | GAG | CTG | GTC | TAC | TTT | GAG | AAG | TCT | CCT | GAC | 1141 |
| Pro | Arg | Arg | Leu | Ser | Gly | Glu | Leu | Val | Tyr | Phe | Glu | Lys | Ser | Pro | Asp | |
| | | | | 305 | | | | | 310 | | | | | 315 | | |
| TTC | TGT | GAG | CGA | GAC | CCC | ACT | ATG | GGC | TCC | CCA | GGG | ACA | AGG | GGC | CGG | 1189 |
| Phe | Cys | Glu | Arg | Asp | Pro | Thr | Met | Gly | Ser | Pro | Gly | Thr | Arg | Gly | Arg | |
| | | | 320 | | | | | 325 | | | | | 330 | | | |
| GCC | TGC | AAC | AAG | ACC | AGC | CGC | CTG | TTG | GAT | GGC | TGT | GGC | AGC | TTG | TGC | 1237 |
| Ala | Cys | Asn | Lys | Thr | Ser | Arg | Leu | Leu | Asp | Gly | Cys | Gly | Ser | Leu | Cys | |
| | | | 335 | | | | 340 | | | | | 345 | | | | |
| TGT | GGG | CGT | GGG | CAC | AAC | GTG | CTC | CGG | CAG | ACA | CGA | GTT | GAG | CGC | TGC | 1285 |
| Cys | Gly | Arg | Gly | His | Asn | Val | Leu | Arg | Gln | Thr | Arg | Val | Glu | Arg | Cys | |
| | | 350 | | | | | 355 | | | | | 360 | | | | |
| CAT | TGC | CGC | TTC | CAC | TGG | TGC | TGC | TAT | GTG | CTG | TGT | GAT | GAG | TGC | AAG | 1333 |
| His | Cys | Arg | Phe | His | Trp | Cys | Cys | Tyr | Val | Leu | Cys | Asp | Glu | Cys | Lys | |
| 365 | | | | | 370 | | | | | 375 | | | | | 380 | |
| GTT | ACA | GAG | TGG | GTG | AAT | GTG | TGT | AAG | TGAGGGTCAG | | CCTTACCTTG | | | | | 1380 |
| Val | Thr | Glu | Trp | Val | Asn | Val | Cys | Lys | | | | | | | | |
| | | | | 385 | | | | | | | | | | | | |

| | | | | |
|---|---|---|---|---|
| GGGCTGGGGA | AGAGGACTGT | GTGAGAGGGG | CCCCTTTTCA | AGCCCTTTGC | TCTTGATTTC | 1440 |
| CTTCCCAAGG | TCACTCTTGG | TCCCTGGAAG | CTTAAAGTAT | CTACCTGGAA | ACAAGCTTTA | 1500 |
| GGGGTGGTGG | GGGTCAGGTG | GACTCTGGGA | TGTGTAGCCT | TCTCCCCAAC | AATTGGAGGG | 1560 |
| TCTTGAGGGG | AAGCTGCCAC | CCCTCTTCTG | CTCCTTAGAC | ACCTGAATGG | ACTAAGATGA | 1620 |
| AATGCACTGT | ATTGCTCCTC | CCACTTCTCA | ACTCCAGCGC | CCCTTTAACC | CTGATTCATA | 1680 |
| CTCCTTTTGG | CTGGGGAGTC | CCTATAGTTT | CACCACTCCT | CTCCCTTGAG | GGATAACCCC | 1740 |
| AGGCACTGTT | TGGAGCCATA | AGATCTGTAT | CTAGAAAGAG | ATCACCCACT | CCTATGTACT | 1800 |
| ATCCCCAAAC | TCCTTTACTG | CAGCCTGGGC | TCCCTCTTGT | GGGATAATGG | GAGACAGTGG | 1860 |
| TAGAGAGGTT | TTTCTTGGGA | AAGAGACAGA | GTTCTGAGGG | GCACTCTCCC | CTGAATCCTC | 1920 |
| AGAGAGTTGT | CTGTCCAGGC | CCTTAGGGAA | GTTGTCTCCT | TCCATTCAGA | TGTTAATGGG | 1980 |
| GACCCTCCCA | AGGAAGGGGT | TTTCCCATGA | CTCTTGGAGC | CTCTTTTCC | TTCTTCAACA | 2040 |
| GGAAGGGTGG | GAAGGGATAA | TTTATCATAC | TGAGACTTGT | TCTTGGTTCC | TGTTTGAAAC | 2100 |
| TAAAATAAAT | TAAGTTACTG | GG | | | | 2122 |

( 2 ) INFORMATION FOR SEQ ID NO:2:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Leu | Glu | Glu | Pro | Arg | Ser | Arg | Ser | Pro | Pro | Ser | Gly | Leu | Ala | Gly |
| 1 | | | | 5 | | | | | 10 | | | | | 15 | |
| Leu | Leu | Phe | Leu | Ala | Leu | Cys | Ser | Arg | Ala | Leu | Ser | Asn | Glu | Ile | Leu |
| | | | 20 | | | | | 25 | | | | | 30 | | |
| Gly | Leu | Lys | Leu | Pro | Gly | Glu | Pro | Pro | Leu | Thr | Gly | Asn | Thr | Val | Cys |
| | | 35 | | | | | 40 | | | | | 45 | | | |
| Leu | Thr | Leu | Ser | Gly | Leu | Ser | Lys | Arg | Gln | Leu | Gly | Leu | Cys | Leu | Arg |
| | 50 | | | | | 55 | | | | | 60 | | | | |
| Asn | Pro | Asp | Val | Thr | Ala | Ser | Ala | Leu | Gln | Gly | Leu | His | Ile | Ala | Val |
| 65 | | | | | 70 | | | | | 75 | | | | | 80 |

| | | | | | | | | | | | | | | |
|---|---|---|---|---|---|---|---|---|---|---|---|---|---|---|
| His | Glu | Cys | Gln | His | Gln | Leu | Arg | Asp | Gln | Arg | Trp | Asn | Cys | Ser | Ala |
| | | | | 85 | | | | | 90 | | | | | 95 | |
| Leu | Glu | Gly | Gly | Gly | Arg | Leu | Pro | His | His | Ser | Ala | Ile | Leu | Lys | Arg |
| | | | | 100 | | | | | 105 | | | | | 110 | |
| Gly | Phe | Arg | Glu | Ser | Ala | Phe | Ser | Phe | Ser | Met | Leu | Ala | Ala | Gly | Val |
| | | | | 115 | | | | | 120 | | | | | 125 | |
| Met | His | Ala | Val | Ala | Thr | Ala | Cys | Ser | Leu | Gly | Lys | Leu | Val | Ser | Cys |
| | | | | 130 | | | | | 135 | | | | | 140 | |
| Gly | Cys | Gly | Trp | Lys | Gly | Ser | Gly | Glu | Gln | Asp | Arg | Leu | Arg | Ala | Lys |
| 145 | | | | | 150 | | | | | 155 | | | | | 160 |
| Leu | Leu | Gln | Leu | Gln | Ala | Leu | Ser | Arg | Gly | Lys | Ser | Phe | Pro | His | Ser |
| | | | | 165 | | | | | 170 | | | | | 175 | |
| Leu | Pro | Ser | Pro | Gly | Pro | Gly | Ser | Ser | Pro | Ser | Pro | Gly | Pro | Gln | Asp |
| | | | | 180 | | | | | 185 | | | | | 190 | |
| Thr | Trp | Glu | Trp | Gly | Gly | Cys | Asn | His | Asp | Met | Asp | Phe | Gly | Glu | Lys |
| | | | | 195 | | | | | 200 | | | | | 205 | |
| Phe | Ser | Arg | Asp | Phe | Leu | Asp | Ser | Arg | Glu | Ala | Pro | Arg | Asp | Ile | Gln |
| | | | | 210 | | | | | 215 | | | | | 220 | |
| Ala | Arg | Met | Arg | Ile | His | Asn | Asn | Arg | Val | Gly | Arg | Gln | Val | Val | Thr |
| 225 | | | | | 230 | | | | | 235 | | | | | 240 |
| Glu | Asn | Leu | Lys | Arg | Lys | Cys | Lys | Cys | His | Gly | Thr | Ser | Gly | Ser | Cys |
| | | | | 245 | | | | | 250 | | | | | 255 | |
| Gln | Phe | Lys | Thr | Cys | Trp | Arg | Ala | Ala | Pro | Glu | Phe | Arg | Ala | Val | Gly |
| | | | | 260 | | | | | 265 | | | | | 270 | |
| Ala | Ala | Leu | Arg | Glu | Arg | Leu | Gly | Arg | Ala | Ile | Phe | Ile | Asp | Thr | His |
| | | | | 275 | | | | | 280 | | | | | 285 | |
| Asn | Arg | Asn | Ser | Gly | Ala | Phe | Gln | Pro | Arg | Leu | Arg | Pro | Arg | Arg | Leu |
| | | | | 290 | | | | | 295 | | | | | 300 | |
| Ser | Gly | Glu | Leu | Val | Tyr | Phe | Glu | Lys | Ser | Pro | Asp | Phe | Cys | Glu | Arg |
| 305 | | | | | 310 | | | | | 315 | | | | | 320 |
| Asp | Pro | Thr | Met | Gly | Ser | Pro | Gly | Thr | Arg | Gly | Arg | Ala | Cys | Asn | Lys |
| | | | | 325 | | | | | 330 | | | | | 335 | |
| Thr | Ser | Arg | Leu | Leu | Asp | Gly | Cys | Gly | Ser | Leu | Cys | Cys | Gly | Arg | Gly |
| | | | | 340 | | | | | 345 | | | | | 350 | |
| His | Asn | Val | Leu | Arg | Gln | Thr | Arg | Val | Glu | Arg | Cys | His | Cys | Arg | Phe |
| | | | | 355 | | | | | 360 | | | | | 365 | |
| His | Trp | Cys | Cys | Tyr | Val | Leu | Cys | Asp | Glu | Cys | Lys | Val | Thr | Glu | Trp |
| | | | | 370 | | | | | 375 | | | | | 380 | |
| Val | Asn | Val | Cys | Lys | | | | | | | | | | | |
| 385 | | | | | | | | | | | | | | | |

( 2 ) INFORMATION FOR SEQ ID NO:3:

( i ) SEQUENCE CHARACTERISTICS:
        ( A ) LENGTH: 1748 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 194..538

( x i ) SEQUENCE DESCRIPTION: SEQ ID NO:3:

```
GAAGCGGTGA AGAGGAGTGG CCCGGCCCTG GAAGAATGCG GCTCTGACAA GGGGACAGAA        60

CCCAGCGCAG TCTCCCCACG GTTTAAGCAG CACTAGTGAA GCCCAGGCAA CCCAACCGTG       120
```

-continued

| | | | | | | | | | | | | | | | | |
|---|---|---|---|---|---|---|---|---|---|---|---|---|---|---|---|---|
| CCTGTCTCGG | ACCCCGCACC | CAAACCACTG | GAGGTCCTGA | TCGATCTGCC | CACCGGAGCC | | | | | | | | | | | 180 |

```
TCCGGGCTTC  GAC  ATG  CTG  GAG  GAG  CCC  CGG  TCG  CGG  TCT  CCG  CCC  TCG         229
             Met  Leu  Glu  Glu  Pro  Arg  Ser  Arg  Ser  Pro  Pro  Ser
                  390                 395                 400

GGC  CTC  GCG  GGT  CTC  CTG  TTC  CTG  GCG  TTG  TGC  AGT  CGG  GCT  CTA  AGC      277
Gly  Leu  Ala  Gly  Leu  Leu  Phe  Leu  Ala  Leu  Cys  Ser  Arg  Ala  Leu  Ser
               405                      410                      415

AAT  GAG  ATT  CTG  GGC  CTG  AAG  TTG  CCT  GGC  GAG  CCG  CCG  CTG  ACG  GGC      325
Asn  Glu  Ile  Leu  Gly  Leu  Lys  Leu  Pro  Gly  Glu  Pro  Pro  Leu  Thr  Gly
               420                      425                      430

AAC  ACC  GTG  TGC  TTG  ACG  CTG  TCC  GGC  CTG  AGC  AAG  CGG  CAG  CTA  GGC      373
Asn  Thr  Val  Cys  Leu  Thr  Leu  Ser  Gly  Leu  Ser  Lys  Arg  Gln  Leu  Gly
               435                      440                      445

CTG  TGC  CTG  CGC  AAC  CCC  GAC  GTG  ACG  GCG  TCC  GCG  CTT  CAG  GGT  CTG      421
Leu  Cys  Leu  Arg  Asn  Pro  Asp  Val  Thr  Ala  Ser  Ala  Leu  Gln  Gly  Leu
450                      455                      460                      465

CAC  ATC  GCG  GTC  CAC  GAG  TGT  CAG  CAC  CAG  CTG  CGC  GAC  CAG  CGC  TGG      469
His  Ile  Ala  Val  His  Glu  Cys  Gln  His  Gln  Leu  Arg  Asp  Gln  Arg  Trp
               470                      475                      480

AAC  TGC  TCC  GCG  CTT  GAG  GGC  GGC  GGC  CGC  CTG  CCG  CAC  CAC  AGC  GCC      517
Asn  Cys  Ser  Ala  Leu  Glu  Gly  Gly  Gly  Arg  Leu  Pro  His  His  Ser  Ala
               485                      490                      495

ATC  CTC  AAG  CGC  GGT  GGT  AAC  TGAAAACCTG  AAGCGGAAAT  GCAAGTGTCA              568
Ile  Leu  Lys  Arg  Gly  Gly  Asn
               500
```

| | | | | | |
|---|---|---|---|---|---|
| TGGCACATCA | GGCAGCTGCC | AGTTCAAGAC | ATGCTGGAGG | GCGGCCCCAG | AGTTCCGGGC | 628 |
| AGTGGGGGCG | GCGTTGAGGG | AACGGCTGGG | CCGGGCCATC | TTCATTGATA | CCCACAACCG | 688 |
| CAATTCTGGA | GCCTTCCAGC | CCCGTCTGCG | TCCCCGTCGC | CTCTCAGGAG | AGCTGGTCTA | 748 |
| CTTTGAGAAG | TCTCCTGACT | TCTGTGAGCG | AGACCCCACT | ATGGGCTCCC | CAGGGACAAG | 808 |
| GGGCCGGGCC | TGCAACAAGA | CCAGCCGCCT | GTTGGATGGC | TGTGGCAGCT | TGTGCTGTGG | 868 |
| GCGTGGGCAC | AACGTGCTCC | GGCAGACACG | AGTTGAGCGC | TGCCATTGCC | GCTTCCACTG | 928 |
| GTGCTGCTAT | GTGCTGTGTG | ATGAGTGCAA | GGTTACAGAG | TGGGTGAATG | TGTGTAAGTG | 988 |
| AGGGTCAGCC | TTACCTTGGG | GCTGGGGAAG | AGGACTGTGT | GAGAGGGGCC | CCTTTTCAAG | 1048 |
| CCCTTTGCTC | TTGATTTCCT | TCCCAAGGTC | ACTCTTGGTC | CCTGGAAGCT | TAAAGTATCT | 1108 |
| ACCTGGAAAC | AAGCTTTAGG | GGTGGTGGGG | GTCAGGTGGA | CTCTGGGATG | TGTAGCCTTC | 1168 |
| TCCCCAACAA | TTGGAGGGTC | TTGAGGGGAA | GCTGCCACCC | CTCTTCTGCT | CCTTAGACAC | 1228 |
| CTGAATGGAC | TAAGATGAAA | TGCACTGTAT | TGCTCCTCCC | ACTTCTCAAC | TCCAGCGCCC | 1288 |
| CTTTAACCCT | GATTCATACT | CCTTTTGGCT | GGGGAGTCCC | TATAGTTTCA | CCACTCCTCT | 1348 |
| CCCTTGAGGG | ATAACCCCAG | GCACTGTTTG | GAGCCATAAG | ATCTGTATCT | AGAAAGAGAT | 1408 |
| CACCCACTCC | TATGTACTAT | CCCCAAACTC | CTTTACTGCA | GCCTGGGCTC | CCTCTTGTGG | 1468 |
| GATAATGGGA | GACAGTGGTA | GAGAGGTTTT | TCTTGGGAAA | GAGACAGAGT | TCTGAGGGGC | 1528 |
| ACTCTCCCCT | GAATCCTCAG | AGAGTTGTCT | GTCCAGGCCC | TTAGGGAAGT | TGTCTCCTTC | 1588 |
| CATTCAGATG | TTAATGGGA | CCCTCCCAAG | GAAGGGGTTT | TCCCATGACT | CTTGGAGCCT | 1648 |
| CTTTTTCCTT | CTTCAACAGG | AAGGGTGGGA | AGGGATAATT | TATCATACTG | AGACTTGTTC | 1708 |
| TTGGTTCCTG | TTTGAAACTA | AAATAAATTA | AGTTACTGGG | | | 1748 |

( 2 ) INFORMATION FOR SEQ ID NO:4:

( i ) SEQUENCE CHARACTERISTICS:
        ( A ) LENGTH: 115 amino acids
        ( B ) TYPE: amino acid (D) TOPOLOGY: linear (ii) MOLECULE TYPE: protein (xi) SEQUENCE DESCRIPTION: SEQ ID NO:4:

| Met | Leu | Glu | Glu | Pro | Arg | Ser | Arg | Ser | Pro | Pro | Ser | Gly | Leu | Ala | Gly |
|---|---|---|---|---|---|---|---|---|---|---|---|---|---|---|---|
| 1 | | | | 5 | | | | | 10 | | | | | 15 | |

| Leu | Leu | Phe | Leu | Ala | Leu | Cys | Ser | Arg | Ala | Leu | Ser | Asn | Glu | Ile | Leu |
|---|---|---|---|---|---|---|---|---|---|---|---|---|---|---|---|
| | | | 20 | | | | 25 | | | | | 30 | | | |

| Gly | Leu | Lys | Leu | Pro | Gly | Glu | Pro | Pro | Leu | Thr | Gly | Asn | Thr | Val | Cys |
|---|---|---|---|---|---|---|---|---|---|---|---|---|---|---|---|
| | | 35 | | | | | 40 | | | | | 45 | | | |

| Leu | Thr | Leu | Ser | Gly | Leu | Ser | Lys | Arg | Gln | Leu | Gly | Leu | Cys | Leu | Arg |
|---|---|---|---|---|---|---|---|---|---|---|---|---|---|---|---|
| | 50 | | | | | 55 | | | | | 60 | | | | |

| Asn | Pro | Asp | Val | Thr | Ala | Ser | Ala | Leu | Gln | Gly | Leu | His | Ile | Ala | Val |
|---|---|---|---|---|---|---|---|---|---|---|---|---|---|---|---|
| 65 | | | | 70 | | | | | 75 | | | | | 80 | |

| His | Glu | Cys | Gln | His | Gln | Leu | Arg | Asp | Gln | Arg | Trp | Asn | Cys | Ser | Ala |
|---|---|---|---|---|---|---|---|---|---|---|---|---|---|---|---|
| | | | | 85 | | | | | 90 | | | | | 95 | |

| Leu | Glu | Gly | Gly | Gly | Arg | Leu | Pro | His | His | Ser | Ala | Ile | Leu | Lys | Arg |
|---|---|---|---|---|---|---|---|---|---|---|---|---|---|---|---|
| | | | 100 | | | | | 105 | | | | | 110 | | |

| Gly | Gly | Asn |
|---|---|---|
| | | 115 |

(2) INFORMATION FOR SEQ ID NO:5:

(i) SEQUENCE CHARACTERISTICS:
        (A) LENGTH: 376 amino acids
        (B) TYPE: amino acid
        (C) STRANDEDNESS: single
        (D) TOPOLOGY: linear (xi) SEQUENCE DESCRIPTION: SEQ ID NO:5:

| Met | Leu | Glu | Glu | Pro | Arg | Ser | Arg | Pro | Pro | Gly | Leu | Ala | Gly | Leu | Leu |
|---|---|---|---|---|---|---|---|---|---|---|---|---|---|---|---|
| 1 | | | | 5 | | | | | 10 | | | | | 15 | |

| Phe | Leu | Ala | Leu | Ser | Arg | Ala | Leu | Ser | Asn | Glu | Ile | Leu | Gly | Leu | Lys |
|---|---|---|---|---|---|---|---|---|---|---|---|---|---|---|---|
| | | | 20 | | | | 25 | | | | | 30 | | | |

| Leu | Pro | Gly | Glu | Pro | Pro | Leu | Thr | Asn | Thr | Val | Cys | Leu | Thr | Leu | Ser |
|---|---|---|---|---|---|---|---|---|---|---|---|---|---|---|---|
| | | 35 | | | | | 40 | | | | | 45 | | | |

| Gly | Leu | Ser | Lys | Arg | Gln | Leu | Gly | Leu | Cys | Leu | Arg | Pro | Asp | Val | Thr |
|---|---|---|---|---|---|---|---|---|---|---|---|---|---|---|---|
| | 50 | | | | | 55 | | | | | 60 | | | | |

| Ala | Ser | Ala | Leu | Gln | Gly | Leu | His | Ile | Ala | Val | His | Glu | Cys | Gln | His |
|---|---|---|---|---|---|---|---|---|---|---|---|---|---|---|---|
| 65 | | | | 70 | | | | | 75 | | | | | 80 | |

| Gln | Leu | Arg | Asp | Gln | Arg | Trp | Asn | Cys | Ser | Ala | Leu | Glu | Gly | Gly | Gly |
|---|---|---|---|---|---|---|---|---|---|---|---|---|---|---|---|
| | | | | 85 | | | | | 90 | | | | | 95 | |

| Arg | Leu | Pro | His | His | Ser | Ala | Ile | Leu | Lys | Arg | Gly | Phe | Arg | Glu | Ser |
|---|---|---|---|---|---|---|---|---|---|---|---|---|---|---|---|
| | | | 100 | | | | | 105 | | | | | 110 | | |

| Ala | Phe | Ser | Phe | Ser | Met | Leu | Ala | Ala | Gly | Val | Met | His | Ala | Val | Ala |
|---|---|---|---|---|---|---|---|---|---|---|---|---|---|---|---|
| | | | 115 | | | | | 120 | | | | | 125 | | |

| Thr | Ala | Cys | Ser | Leu | Gly | Lys | Leu | Val | Ser | Cys | Gly | Cys | Gly | Trp | Lys |
|---|---|---|---|---|---|---|---|---|---|---|---|---|---|---|---|
| | 130 | | | | | 135 | | | | | 140 | | | | |

| Gly | Ser | Gly | Glu | Gln | Asp | Arg | Leu | Arg | Ala | Lys | Leu | Leu | Gln | Leu | Gln |
|---|---|---|---|---|---|---|---|---|---|---|---|---|---|---|---|
| 145 | | | | | 150 | | | | | 155 | | | | | 160 |

| Ala | Leu | Ser | Arg | Gly | Lys | Phe | Pro | Ser | Pro | Ser | Pro | Gly | Ser | Pro |
|---|---|---|---|---|---|---|---|---|---|---|---|---|---|---|
| | | | | 165 | | | | | 170 | | | | | 175 |

| Ser | Pro | Gly | Pro | Gln | Asp | Thr | Trp | Glu | Trp | Gly | Gly | Cys | Asn | His | Asp |
|---|---|---|---|---|---|---|---|---|---|---|---|---|---|---|---|
| | | | | 180 | | | | | 185 | | | | | 190 | |

| Met | Asp | Phe | Gly | Glu | Lys | Phe | Ser | Arg | Asp | Phe | Leu | Asp | Ser | Arg | Glu |
|---|---|---|---|---|---|---|---|---|---|---|---|---|---|---|---|
| | | | 195 | | | | | 200 | | | | | 205 | | |

```
Ala  Pro  Arg  Asp  Ile  Gln  Ala  Arg  Met  Arg  Ile  His  Asn  Asn  Arg  Val
     210                      215                      220

Gly  Arg  Gln  Val  Val  Thr  Glu  Asn  Leu  Lys  Arg  Lys  Cys  Lys  Cys  His
225                      230                      235                      240

Gly  Thr  Ser  Gly  Ser  Cys  Gln  Phe  Lys  Thr  Cys  Trp  Arg  Ala  Ala  Pro
               245                      250                           255

Glu  Phe  Arg  Ala  Gly  Ala  Ala  Leu  Arg  Glu  Arg  Leu  Arg  Ala  Ile  Phe
               260                      265                      270

Ile  Asp  Thr  His  Asn  Arg  Asn  Ser  Gly  Ala  Phe  Gln  Pro  Arg  Leu  Arg
          275                      280                      285

Pro  Arg  Arg  Leu  Ser  Gly  Glu  Leu  Val  Tyr  Phe  Glu  Lys  Ser  Pro  Asp
     290                      295                      300

Phe  Cys  Glu  Arg  Asp  Pro  Thr  Gly  Ser  Pro  Gly  Thr  Arg  Gly  Arg  Ala
305                      310                      315                      320

Cys  Asn  Lys  Thr  Ser  Arg  Leu  Leu  Asp  Gly  Cys  Gly  Ser  Leu  Cys  Cys
               325                      330                      335

Gly  Arg  Gly  His  Asn  Val  Leu  Arg  Gln  Thr  Arg  Val  Glu  Arg  Cys  His
               340                      345                      350

Cys  Arg  Phe  His  Trp  Cys  Cys  Tyr  Val  Leu  Cys  Asp  Glu  Cys  Lys  Val
               355                      360                      365

Thr  Glu  Trp  Val  Asn  Val  Cys  Lys
     370                      375
```

( 2 ) INFORMATION FOR SEQ ID NO:6:

( i ) SEQUENCE CHARACTERISTICS:
    ( A ) LENGTH: 389 amino acids
    ( B ) TYPE: amino acid
    ( C ) STRANDEDNESS: single
    ( D ) TOPOLOGY: linear ( x i ) SEQUENCE DESCRIPTION: SEQ ID NO:6:

```
Met  Leu  Glu  Glu  Pro  Arg  Ser  Arg  Pro  Pro  Leu  Gly  Leu  Ala  Gly
1                   5                    10                       15

Leu  Leu  Phe  Leu  Ala  Leu  Phe  Ser  Arg  Ala  Leu  Ser  Asn  Glu  Ile  Leu
               20                       25                       30

Gly  Leu  Lys  Leu  Pro  Gly  Glu  Pro  Pro  Leu  Thr  Ala  Asn  Thr  Val  Cys
          35                       40                       45

Leu  Thr  Leu  Ser  Gly  Leu  Ser  Lys  Arg  Gln  Leu  Gly  Leu  Cys  Leu  Arg
     50                       55                       60

Ser  Pro  Asp  Val  Thr  Ala  Ser  Ala  Leu  Gln  Gly  Leu  His  Ile  Ala  Val
65                       70                       75                       80

His  Glu  Cys  Gln  His  Gln  Leu  Arg  Asp  Gln  Arg  Trp  Asn  Cys  Ser  Ala
                    85                       90                       95

Leu  Glu  Gly  Gly  Gly  Arg  Leu  Pro  His  His  Ser  Ala  Ile  Leu  Lys  Arg
                    100                      105                      110

Gly  Phe  Arg  Glu  Ser  Ala  Phe  Ser  Phe  Ser  Met  Leu  Ala  Ala  Gly  Val
          115                      120                      125

Met  His  Ala  Val  Ala  Thr  Ala  Cys  Ser  Leu  Gly  Lys  Leu  Val  Ser  Cys
     130                      135                      140

Gly  Cys  Gly  Trp  Lys  Gly  Ser  Gly  Glu  Gln  Asp  Arg  Leu  Arg  Ala  Lys
145                      150                      155                      160

Leu  Leu  Gln  Leu  Gln  Ala  Leu  Ser  Arg  Gly  Lys  Ile  Phe  Pro  Ile  Ser
                    165                      170                      175

Gln  Pro  Ser  Pro  Val  Pro  Gly  Ser  Val  Pro  Ser  Pro  Gly  Pro  Gln  Asp
               180                      185                      190
```

```
Thr Trp Glu Trp Gly Gly Cys Asn His Asp Met Asp Phe Gly Glu Lys
    195             200             205

Phe Ser Arg Asp Phe Leu Asp Ser Arg Glu Ala Pro Arg Asp Ile Gln
    210             215             220

Ala Arg Met Arg Ile His Asn Asn Arg Val Gly Arg Gln Val Val Thr
225             230             235                             240

Glu Asn Leu Lys Arg Lys Cys Lys Cys His Gly Thr Ser Gly Ser Cys
                245             250             255

Gln Phe Lys Thr Cys Trp Arg Ala Ala Pro Glu Phe Arg Ala Ile Gly
            260             265             270

Ala Ala Leu Arg Glu Arg Leu Ser Arg Ala Ile Phe Ile Asp Thr His
        275             280             285

Asn Arg Asn Ser Gly Ala Phe Gln Pro Arg Leu Arg Pro Arg Arg Leu
    290             295             300

Ser Gly Glu Leu Val Tyr Phe Glu Lys Ser Pro Asp Phe Cys Glu Arg
305             310             315                             320

Asp Pro Thr Leu Gly Ser Pro Gly Thr Arg Gly Arg Ala Cys Asn Lys
                325             330             335

Thr Ser Arg Leu Leu Asp Gly Cys Gly Ser Leu Cys Cys Gly Arg Gly
            340             345             350

His Asn Val Leu Arg Gln Thr Arg Val Glu Arg Cys His Cys Arg Phe
        355             360             365

His Trp Cys Cys Tyr Val Leu Cys Asp Glu Cys Lys Val Thr Glu Trp
    370             375             380

Val Asn Val Cys Lys
385
```

( 2 ) INFORMATION FOR SEQ ID NO:7:

( i ) SEQUENCE CHARACTERISTICS:
        ( A ) LENGTH: 389 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Met Leu Glu Glu Pro Arg Ser Arg Ser Pro Pro Ser Gly Leu Ala Gly
1               5               10              15

Leu Leu Phe Leu Ala Leu Cys Ser Arg Ala Leu Ser Asn Glu Ile Leu
            20              25              30

Gly Leu Lys Leu Pro Gly Glu Pro Pro Leu Thr Gly Asn Thr Val Cys
        35              40              45

Leu Thr Leu Ser Gly Leu Ser Lys Arg Gln Leu Gly Leu Cys Leu Arg
    50              55              60

Asn Pro Asp Val Thr Ala Ser Ala Leu Gln Gly Leu His Ile Ala Val
65              70              75                              80

His Glu Cys Gln His Gln Leu Arg Asp Gln Arg Trp Asn Cys Ser Ala
                85              90              95

Leu Glu Gly Gly Gly Arg Leu Pro His His Ser Ala Ile Leu Lys Arg
            100             105             110

Gly Phe Arg Glu Ser Ala Phe Ser Phe Ser Met Leu Ala Ala Gly Val
        115             120             125

Met His Ala Val Ala Thr Ala Cys Ser Leu Gly Lys Leu Val Ser Cys
    130             135             140

Gly Cys Gly Trp Lys Gly Ser Gly Glu Gln Asp Arg Leu Arg Ala Lys
145             150             155                             160
```

-continued

| | | | | | | | | | | | | | | |
|---|---|---|---|---|---|---|---|---|---|---|---|---|---|---|
| Leu | Leu | Gln | Leu | Gln<br>165 | Ala | Leu | Ser | Arg | Gly<br>170 | Lys | Ser | Phe | Pro | His<br>175 | Ser |
| Leu | Pro | Ser | Pro<br>180 | Gly | Pro | Gly | Ser | Ser<br>185 | Pro | Ser | Pro | Gly | Pro<br>190 | Gln | Asp |
| Thr | Trp | Glu<br>195 | Trp | Gly | Gly | Cys | Asn<br>200 | His | Asp | Met | Asp | Phe<br>205 | Gly | Glu | Lys |
| Phe | Ser<br>210 | Arg | Asp | Phe | Leu | Asp<br>215 | Ser | Arg | Glu | Ala | Pro<br>220 | Arg | Asp | Ile | Gln |
| Ala<br>225 | Arg | Met | Arg | Ile | His<br>230 | Asn | Asn | Arg | Val | Gly<br>235 | Arg | Gln | Val | Val | Thr<br>240 |
| Glu | Asn | Leu | Lys | Arg<br>245 | Lys | Cys | Lys | Cys | His<br>250 | Gly | Thr | Ser | Gly | Ser<br>255 | Cys |
| Gln | Phe | Lys | Thr<br>260 | Cys | Trp | Arg | Ala | Ala<br>265 | Pro | Glu | Phe | Arg | Ala<br>270 | Val | Gly |
| Ala | Ala | Leu<br>275 | Arg | Glu | Arg | Leu | Gly<br>280 | Arg | Ala | Ile | Phe | Ile<br>285 | Asp | Thr | His |
| Asn | Arg<br>290 | Asn | Ser | Gly | Ala | Phe<br>295 | Gln | Pro | Arg | Leu | Arg<br>300 | Pro | Arg | Arg | Leu |
| Ser<br>305 | Gly | Glu | Leu | Val | Tyr<br>310 | Phe | Glu | Lys | Ser | Pro<br>315 | Asp | Phe | Cys | Glu | Arg<br>320 |
| Asp | Pro | Thr | Met | Gly<br>325 | Ser | Pro | Gly | Thr | Arg<br>330 | Gly | Arg | Ala | Cys | Asn<br>335 | Lys |
| Thr | Ser | Arg | Leu<br>340 | Leu | Asp | Gly | Cys | Gly<br>345 | Ser | Leu | Cys | Cys | Gly<br>350 | Arg | Gly |
| His | Asn | Val<br>355 | Leu | Arg | Gln | Thr | Arg<br>360 | Val | Glu | Arg | Cys | His<br>365 | Cys | Arg | Phe |
| His | Trp<br>370 | Cys | Cys | Tyr | Val | Leu<br>375 | Cys | Asp | Glu | Cys | Lys<br>380 | Val | Thr | Glu | Trp |
| Val<br>385 | Asn | Val | Cys | Lys | | | | | | | | | | | |

What is claimed is:

1. A non-naturally occurring polynucleotide encoding human Wnt-10b or human Wnt-10bΔ, wherein the polynucleotide has at least 90% sequence identity with the nucleotide sequence depicted in SEQ ID NO:1 or SEQ ID NO:3.

2. An isolated naturally occurring polynucleotide encoding human Wnt-10b or human Wnt-10bΔ, wherein the polynucleotide has at least 90% sequence identity with the nucleotide sequence depicted in SEQ ID NO:1 or SEQ ID NO:3.

3. A recombinant polynucleotide having the nucleotide sequence depicted in Seq. I.D. No. 1 or Seq. I.D. No. 3 or a fragment of at least 100 bases thereof.

4. A recombinant polynucleotide having a nucleic acid sequence with at least 90% sequence identity with the nucleotide sequence depicted in Seq. ID No. 1 or Seq. ID No. 3 or a fragment of at least 100 bases thereof.

5. A recombinant polynucleotide complementary to the nucleic acid sequence depicted in Seq. I.D. No. 1 or Seq. I.D. No. 3 or a fragment of at least 100 bases thereof.

6. A recombinant polynucleotide having a nucleotide sequence with at least 90% sequence identity with of complementary to the nucleic acid sequence depicted in Seq. I.D. No. 1 or Seq. I.D. No. 3, or a fragment of at least 100 bases thereof.

7. A polynucleotide comprising at least 100 bases of the sequence depicted in Seq. I.D. No. 1 or Seq. I.D. No. 3, provided that the polynucleotide does not consist of an identical nucleotide sequence which encodes mouse Wnt10-b.

8. A recombinant polynucleotide encoding a polypeptide having the amino acid sequence depicted in Seq. I.D. No. 2 or Seq. I.D. No. 4 or a fragment of at least 100 bases thereof.

9. A vector comprising the polynucleotide of any of claims 1 to 8.

10. A host cell comprising the polynucleotide of any of claims 1 to 8.

11. A plasmid deposited under ATCC Accession No. 97208, said plasmid comprising a polynucleotide having a sequence depicted in SEQ ID NO: 1 encoding human Wnt-10b.

12. A plasmid deposited under ATCC Accession No. 97207, said plasmid comprising a polynucleotide having a sequence depicted in SEQ ID NO:3 encoding human Wnt-10bΔ.

13. A composition comprising a polynucleotide of any of claims 1 to 8, and a solid or liquid.

* * * * *